(12) United States Patent
Schaeffer et al.

(10) Patent No.: US 10,055,984 B1
(45) Date of Patent: Aug. 21, 2018

(54) UNMANNED AERIAL VEHICLE SYSTEM AND METHOD OF USE

(71) Applicants: Lee Schaeffer, Frisco, TX (US); Norman Seals, Dallas, TX (US); James Nelson Dearien, II, Frisco, TX (US); William Jennings Dearian, Frisco, TX (US)

(72) Inventors: Lee Schaeffer, Frisco, TX (US); Norman Seals, Dallas, TX (US); James Nelson Dearien, II, Frisco, TX (US); William Jennings Dearian, Frisco, TX (US)

(*) Notice: Subject to any disclaimer, the term of this patent is extended or adjusted under 35 U.S.C. 154(b) by 0 days.

(21) Appl. No.: 15/783,351

(22) Filed: Oct. 13, 2017

Related U.S. Application Data

(60) Provisional application No. 62/407,625, filed on Oct. 13, 2016.

(51) Int. Cl.

| | |
|---|---|
| *G08G 1/095* | (2006.01) |
| *G08G 1/09* | (2006.01) |
| *B64C 39/02* | (2006.01) |
| *B64D 47/08* | (2006.01) |
| *B60L 11/18* | (2006.01) |
| *G08G 1/04* | (2006.01) |
| *G08G 1/048* | (2006.01) |
| *A61B 5/01* | (2006.01) |
| *A61B 5/024* | (2006.01) |

(52) U.S. Cl.
CPC ............ *G08G 1/09* (2013.01); *B60L 11/1824* (2013.01); *B64C 39/024* (2013.01); *B64D 47/08* (2013.01); *G08G 1/04* (2013.01); *G08G 1/048* (2013.01); *A61B 5/01* (2013.01); *A61B 5/024* (2013.01); *B60L 2200/10* (2013.01); *B64C 2201/12* (2013.01); *B64C 2201/127* (2013.01); *B64C 2201/128* (2013.01)

(58) Field of Classification Search
CPC ........................................................ G08G 1/09
USPC ........................................................ 340/908
See application file for complete search history.

(56) References Cited

U.S. PATENT DOCUMENTS

| | | | | |
|---|---|---|---|---|
| 9,387,928 | B1* | 7/2016 | Gentry | B64C 39/024 |
| 9,643,722 | B1* | 5/2017 | Myslinski | B64C 39/024 |
| 2014/0018979 | A1* | 1/2014 | Goossen | G08G 5/0034 |
| | | | | 701/3 |

(Continued)

*Primary Examiner* — Santiago Garcia
(74) *Attorney, Agent, or Firm* — Eldredge Law Firm, LLC; Richard G Eldredge

(57) ABSTRACT

An unmanned aerial vehicle (UAV) system includes a command center having a computing device an unmanned aerial vehicle (UAV) with a body, the UAV to communicate wirelessly with the command center via a network, the UAV having a control system with a power source, a geospatial tracking device, and a multi-channel communication portal; a camera secured to the body and in communication with the control system; and one or more equipment attachment sites; site assessment tools to attach to or within the one or more equipment attachment sites, each of the site assessment tools to record a data associated with an emergency site, such as weather conditions, road conditions, traffic, visibility, radiation, and chemical exposure; the UAV is to receive commands from the command center to deploy to the emergency site; and the UAV is to receive the data and transmit the data to the command center via the multi-channel communication portal.

10 Claims, 6 Drawing Sheets

(56) References Cited

U.S. PATENT DOCUMENTS

| | | | |
|---|---|---|---|
| 2014/0241239 A1* | 8/2014 | Chang | H04B 7/18506 370/316 |
| 2016/0111006 A1* | 4/2016 | Srivastava | G08G 1/00 701/3 |
| 2016/0196525 A1* | 7/2016 | Kantor | G08G 5/0013 705/330 |
| 2016/0216711 A1* | 7/2016 | Srivastava | B64D 1/02 |
| 2017/0069214 A1* | 3/2017 | Dupray | G08G 5/0021 |
| 2017/0222712 A1* | 8/2017 | Chang | H04W 4/90 |
| 2017/0278408 A1* | 9/2017 | Gordon | G08G 5/0069 |
| 2017/0313418 A1* | 11/2017 | Yoon | B64C 39/024 |
| 2017/0345282 A1* | 11/2017 | Farrell | G08B 13/02 |
| 2017/0372256 A1* | 12/2017 | Kantor | H04W 4/046 |
| 2018/0024236 A1* | 1/2018 | Zorea | G01S 13/91 |
| 2018/0027772 A1* | 2/2018 | Gordon | A01K 15/023 |
| 2018/0028364 A1* | 2/2018 | Erickson | A61F 13/00085 |
| 2018/0033320 A1* | 2/2018 | Castelli | G08G 5/065 |
| 2018/0061235 A1* | 3/2018 | Goldberg | G08G 1/161 |
| 2018/0102832 A1* | 4/2018 | Chang | H04B 7/18506 |

\* cited by examiner

US 10,055,984 B1

UNMANNED AERIAL VEHICLE SYSTEM AND METHOD OF USE

BACKGROUND

1. Field of the Invention

The present invention relates generally to emergency response systems, and more specifically, to an unmanned aerial vehicle (UAV) system for facilitating real-time communication between an emergency site and emergency responders.

2. Description of Related Art

Emergency response systems are well known in the art and are effective means to aid victims of emergency situations. For example, FIG. 1 depicts a conventional emergency response system 101 having an emergency site 103, emergency responders 105, and a medical facility 107, all in cellular communication 109.

In FIG. 2, a flowchart 201 depicts the method of system 101. The responders 105 receive an alert regarding the emergency site 103 and respond to the alert, as shown with boxes 203, 205. The responders 105 arrive on the site 103 and treat injuries or transport victims to the medical facility 107, as shown with boxes 207, 209, 211. It should be appreciated that conventional communication requires calling via a cell phone.

One of the problems commonly associated with system 101 is limited information and slow response. For example, the emergency responders 105 have little or no information about the emergency site 103 before arriving. In addition, the emergency responders 105 may not arrive promptly, thereby increasing the potential for greater injury or damage.

Accordingly, although great strides have been made in the area of emergency response systems, many shortcomings remain.

DESCRIPTION OF THE DRAWINGS

The novel features believed characteristic of the embodiments of the present application are set forth in the appended claims. However, the embodiments themselves, as well as a preferred mode of use, and further objectives and advantages thereof, will best be understood by reference to the following detailed description when read in conjunction with the accompanying drawings, wherein:

Figure 1:
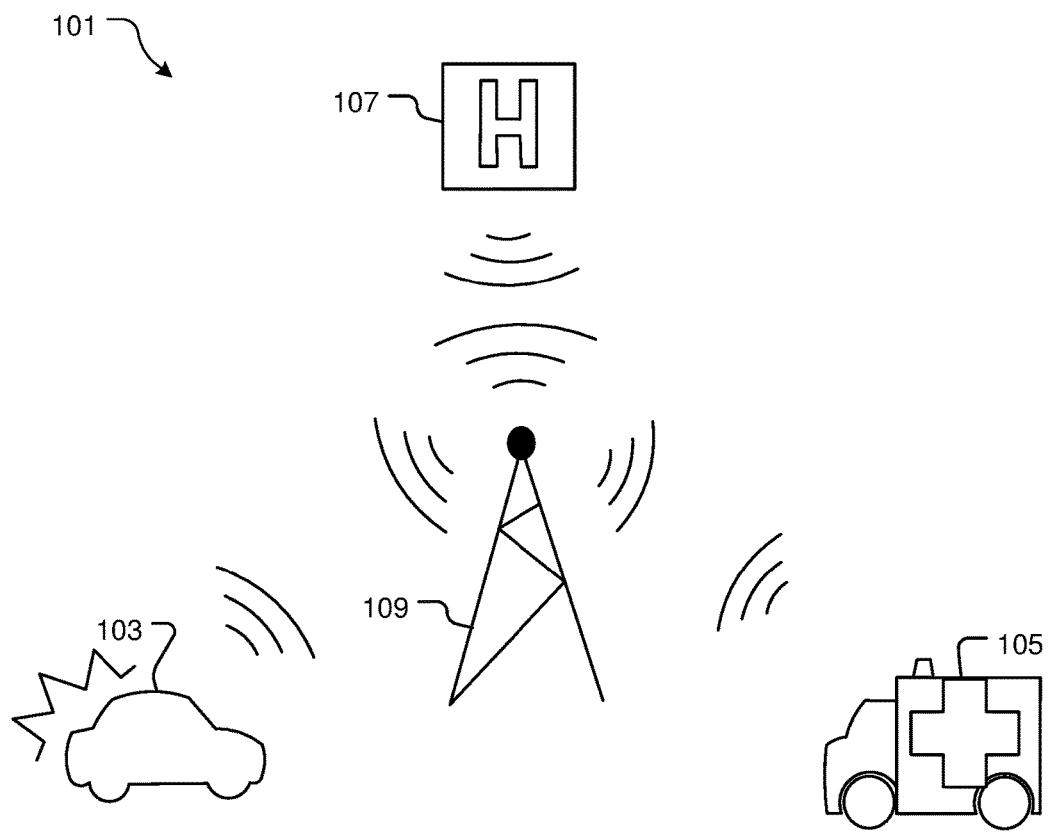
FIG. 1 is a simplified diagram of a common emergency response system.
Figure 2:
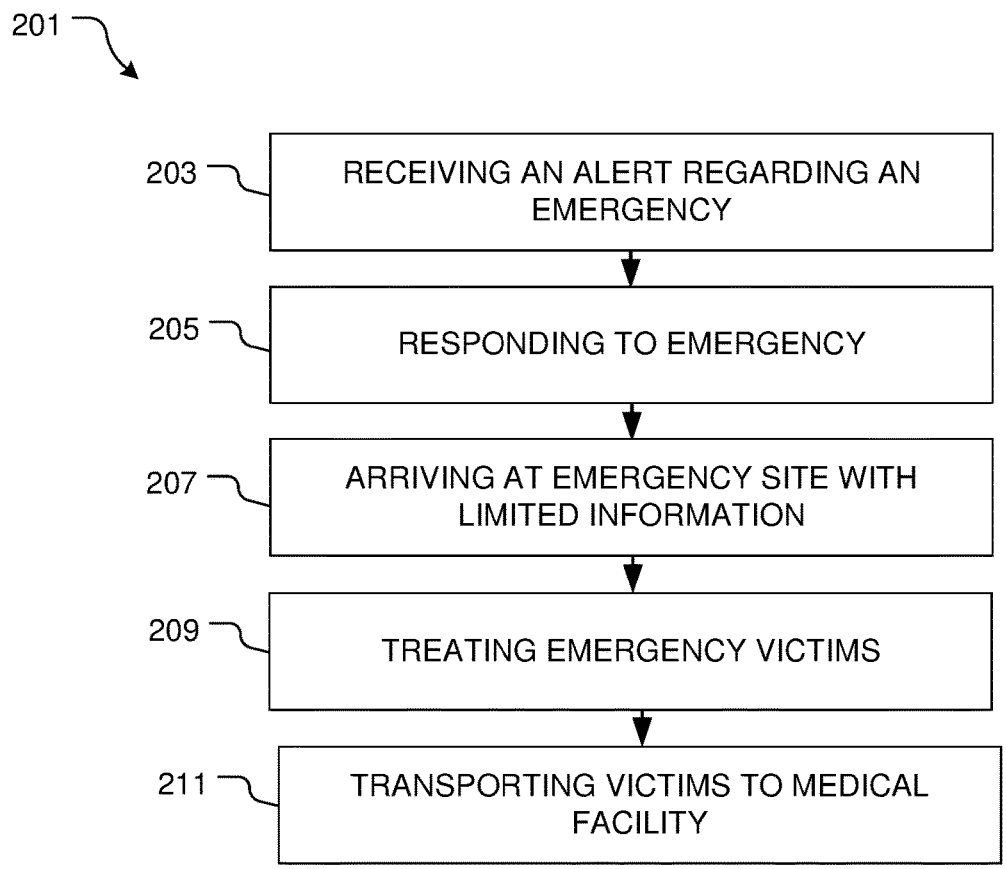
FIG. 2 is a flowchart of the method of FIG. 1.

While the system and method of use of the present application is susceptible to various modifications and alternative forms, specific embodiments thereof have been shown by way of example in the drawings and are herein described in detail. It should be understood, however, that the description herein of specific embodiments is not intended to limit the invention to the particular embodiment disclosed, but on the contrary, the intention is to cover all modifications, equivalents, and alternatives falling within the spirit and scope of the present application as defined by the appended claims.

DETAILED DESCRIPTION OF THE PREFERRED EMBODIMENT

Illustrative embodiments of the system and method of use of the present application are provided below. It will of course be appreciated that in the development of any actual embodiment, numerous implementation-specific decisions will be made to achieve the developer's specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure.

The system and method of use in accordance with the present application overcomes one or more of the above-discussed problems commonly associated with conventional emergency response systems. Specifically, the present invention provides real-time information sharing between emergency responders, on-site personnel, and medical professionals for faster and more effective emergency response. These and other unique features of the system and method of use are discussed below and illustrated in the accompanying drawings.

The system and method of use will be understood, both as to its structure and operation, from the accompanying drawings, taken in conjunction with the accompanying description. Several embodiments of the system are presented herein. It should be understood that various components, parts, and features of the different embodiments may be combined together and/or interchanged with one another, all of which are within the scope of the present application, even though not all variations and particular embodiments are shown in the drawings. It should also be understood that the mixing and matching of features, elements, and/or functions between various embodiments is expressly contemplated herein so that one of ordinary skill in the art would appreciate from this disclosure that the features, elements, and/or functions of one embodiment may be incorporated into another embodiment as appropriate, unless described otherwise.

The preferred embodiment herein described is not intended to be exhaustive or to limit the invention to the precise form disclosed. It is chosen and described to explain the principles of the invention and its application and practical use to enable others skilled in the art to follow its teachings.

Figure 3:
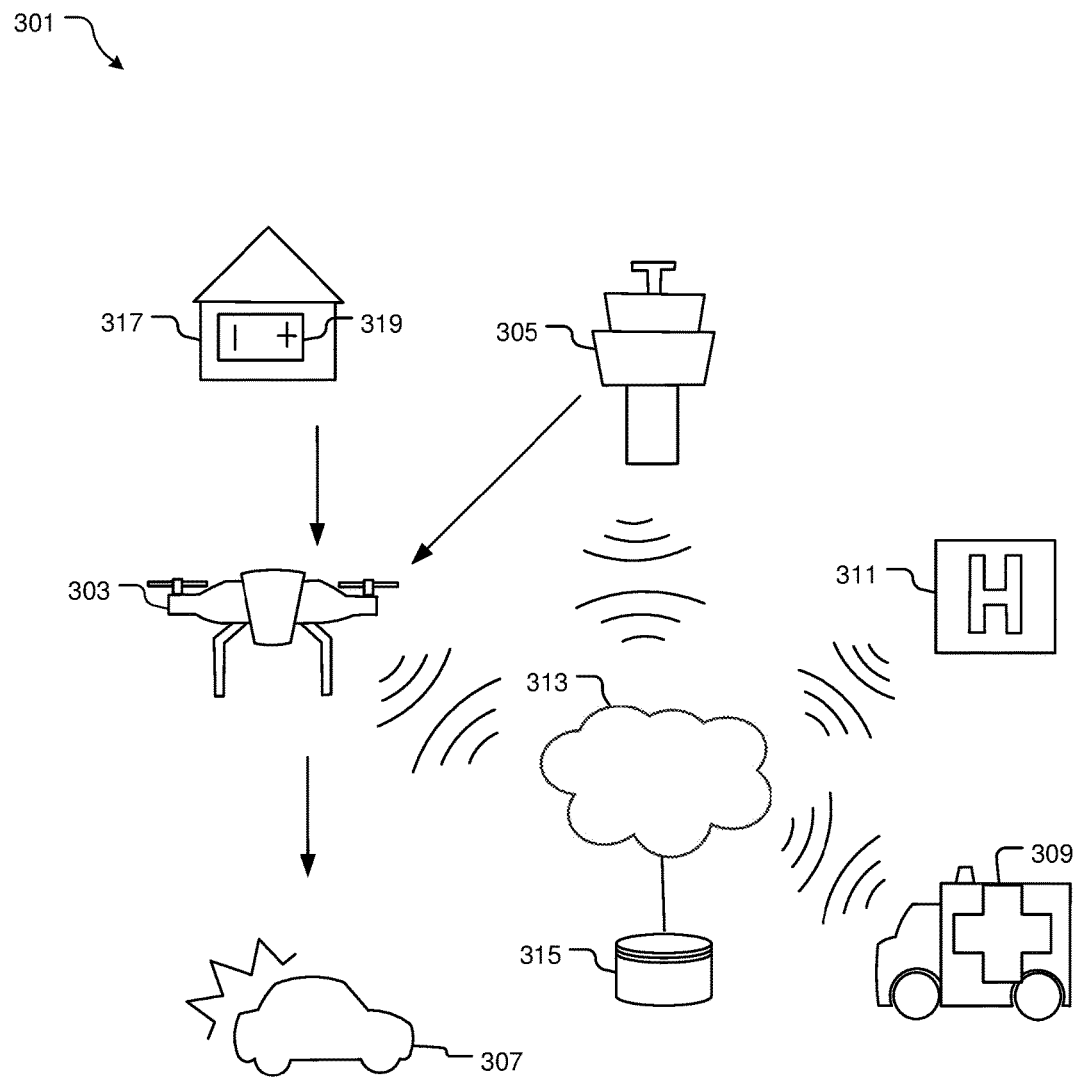
FIG. 3 is a simplified diagram of an unmanned aerial vehicle system in accordance with a preferred embodiment of the present application.

Referring now to the drawings wherein like reference characters identify corresponding or similar elements throughout the several views, FIG. 3 depicts a simplified schematic of an unmanned aerial vehicle system in accordance with a preferred embodiment of the present application. It will be appreciated that system 301 overcomes one or more of the above-listed problems commonly associated with conventional emergency response systems.

In the contemplated embodiment, system 301 includes un unmanned aerial vehicle (UAV) 303 in communication with a command center 305 having one or more servers and computing devices, wherein the command center 305 dispatches the UAV 303 to an emergency site 307, and the UAV 303 facilitates real-time interactions between the site 307, emergency responders 309, and medical professionals 311, via a cloud based wireless network 313. It should be understood that the UAV includes appropriate communication technology and control technology, such as cellular or radio network communication, internal compassing, tilt and gyro sensors, and intelligent flight controllers.

In the preferred embodiment, the cloud based wireless network 313 stores data collected from the site 307 and provides a database 315 of medical information to the site 307, wherein the database of medical information provides information commonly required for treatment of persons in emergency situations. In addition, in the contemplated embodiment, the UAV 303 is housed and charged in an unmanned aerial vehicle nest 317, having a charging port 319.

Figure 4:
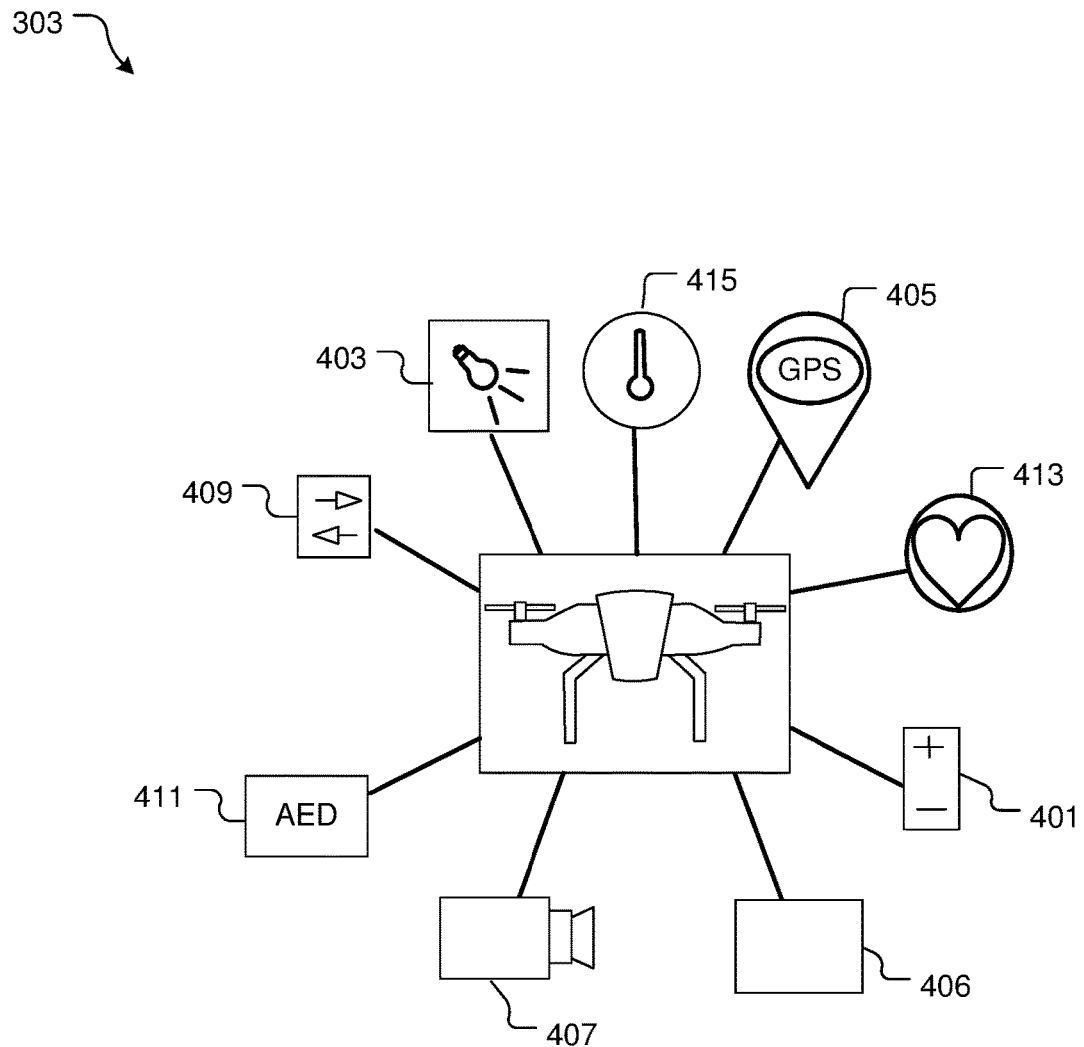
FIG. 4 is a simplified diagram of the features of the unmanned aerial vehicle from FIG. 3.

In FIG. 4 a simplified schematic of some of the contemplated features of the UAV 303 is shown. It should be understood that the UAV can include some or all of the features included herein, or, in addition, could include additional features necessary to function. In the contemplated embodiment, the UAV 303 includes a power source 401, a light 403, a geospatial tracking mechanism 405, a display screen 406, a camera 407, a multi-channel communication portal 409, a plurality of medical equipment attachment sites 411, a plurality of patient monitoring tools 413, and a plurality of site assessment tools 415. It should be appreciated that the plurality of features can be incorporated into the UAV 303 in various ways by those in the art, while still maintaining the same functionality. It should further be appreciated that the UAV can include a central control center configured to receive commands and operate the various features accordingly.

In the preferred embodiment, the display screen 406, camera 407, and multi-channel communication portal 409 are utilized to facilitate information sharing between the parties via a wireless network. Such information can include medical information from database 315 to present to one or more persons on site, thereby providing the one or more persons with necessary emergency and/or medical information. In addition, the plurality of medical equipment attachment sites 411 are utilized to transport medical/emergency equipment, such as a defibrillator, a tourniquet, an epinephrine injection device, and/or a wound care kit to the emergency site 307. It should be appreciated that the attachment sites could be hooks for securing to a clip or other similar fastener, or alternatively, could be a cubby or compartment on the body of the UAV for receiving items. The plurality of patient monitoring tools 413 are utilized to record patient information such as heart rate and/or temperature. It should be appreciated that these monitoring tools can further be stored via compartments or the like within the body of the UAV. It is further contemplated that the plurality of site assessment tools 415 can include tools for monitoring weather, road conditions, traffic, visibility, and radiation and chemical exposure.

It should be appreciated that one of the unique features believed characteristic of the present application is ability of the UAV 303 to facilitate real-time communication and information sharing between the parties. It should be understood that this function is achieved through the combination of features incorporated into the UAV 303. It should be appreciated that this function allows for on-site personnel to receive advice from medical and emergency professionals, as well as provides a means for the medical and emergency professionals to have information about the site before arriving, thereby improving efficiency of an emergency response.

Figure 5:
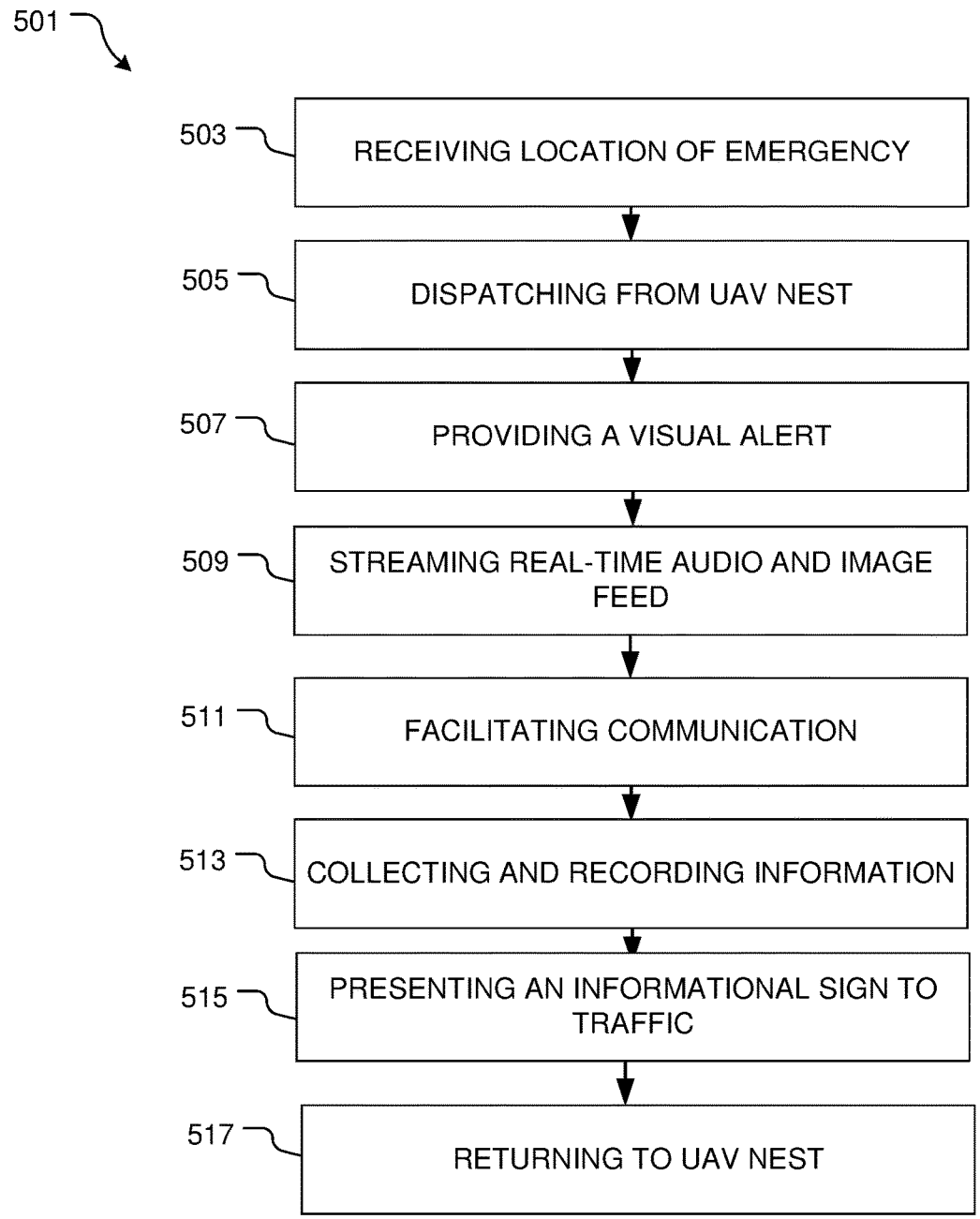
FIG. 5 is a flowchart of the method of FIG. 3.

In FIG. 5, a flowchart 501 depicts the method of system 301. The UAV 303 receives emergency location information from the command center 305 and dispatches from the UAV nest 317, as shown with boxes 503, 505. Once the UAV 303 arrives at the site 307, the UAV 303 provides a visual alert, such as a flashing light, and begins providing real-time audio and video streaming to emergency and medical professionals, as well as facilitating communication via the multi-channel communication portal 409, as shown with boxes 507, 509, 511. The UAV 303 further records patient and site information, as shown with box 513. If necessary, the UAV 303 presents an informational sign to nearby traffic, via the display screen 406, as shown with box 515. When the emergency subsides, the UAV 303 returns to the UAV nest 317 for recharging and storage, as shown with box 517.

Figure 6:
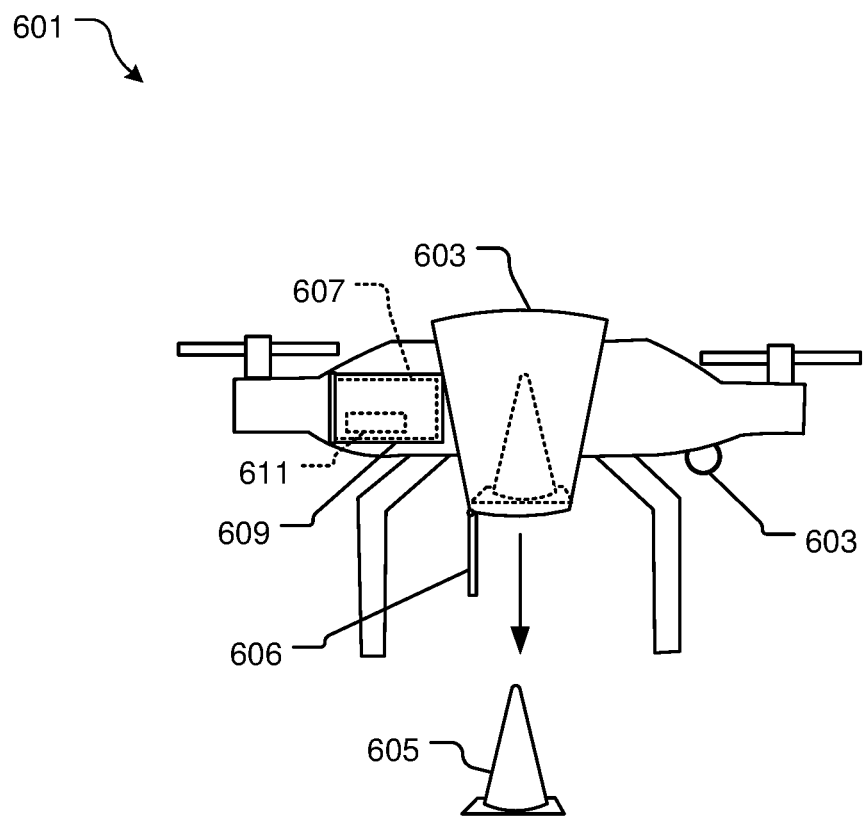
FIG. 6 is an alternative embodiment of the unmanned aerial vehicle from FIG. 3.

In FIG. 6 an embodiment of a UAV 601 is shown, wherein the UAV 601 comprises a traffic cone storage compartment 603 configured to hold a plurality of traffic cones 605 and the UAV 601 is utilized to deploy the traffic cones 605 through an opening having a door 606 and around the emergency site 307 based on commands received from the command center 305. It should be appreciated that this function reduces danger to the emergency responders 309 by diverting traffic before the responders 309 arrive on site 307.

UAV 601 can further include one or more storage compartments 607 accessible via a door 609 and configured to hold one tools 611 such as patient monitoring tools, site assessment tools, and/or medical equipment.

The particular embodiments disclosed above are illustrative only, as the embodiments may be modified and practiced in different but equivalent manners apparent to those skilled in the art having the benefit of the teachings herein. It is therefore evident that the particular embodiments disclosed above may be altered or modified, and all such variations are considered within the scope and spirit of the application. Accordingly, the protection sought herein is as set forth in the description. Although the present embodiments are shown above, they are not limited to just these embodiments, but are amenable to various changes and modifications without departing from the spirit thereof.

What is claimed is:
1. An unmanned aerial vehicle (UAV) system, comprising:
    a command center having a computing device;
    an unmanned aerial vehicle (UAV) with a body the UAV configured to communicate wirelessly with the command center via a network, the UAV having:
        a control system with a power source, a geospatial tracking device, and a multi-channel communication portal;
        a camera secured to the body and in communication with the control system;
        one or more equipment attachment sites;
        a traffic cone storage compartment;
        a plurality of traffic cones; and
        wherein the UAV is configured to deploy one or more traffic cones at the emergency site based on a command from the command center;
    a plurality of site assessment tools configured to attach to or within the one or more equipment attachment sites, each of the plurality of site assessment tools configured to record a data associated with an emergency site, such as weather conditions, road conditions, traffic, visibility, radiation, and chemical exposure;
    wherein the UAV is configured to receive commands from the command center to deploy to the emergency site; and wherein the UAV is configured to receive the data and transmit the data to the command center via the multi-channel communication portal.

2. The system of claim 1, further comprising:
a UAV nest configured to store the UAV and having a charging port configured to charging the power source of the UAV.

3. The system of claim 1, wherein the UAV further comprises:
a display screen in communication with the control center, the display screen configured to present a visual of information at the emergency site.

4. The system of claim 1, wherein the one or more equipment attachment sites is a compartment in the body of the UAV with access via a door.

5. The system of claim 1, further comprising:
a plurality of medical tools configured to secure to or within the one or more equipment attachment sites.

6. The system of claim 1, further comprising:
a plurality of patient monitoring tools configured to be transported via the UAV and in communication with the control center;
wherein the plurality of patient monitoring tools provide data relating to one or more patients at the scene to be transmitted to the command center.

7. The system of claim 1, wherein the camera further comprises:
an infra-red and/or thermal image mechanism; and
wherein the infra-red and/or thermal image mechanism defines hot spots in structure fires to be transmitted to the command center.

8. The system of claim 1, wherein the light is a strobe light configured to flash upon a command from the command center.

9. A method of emergency response, comprising:
providing the system of claim 1;
receiving location information of an emergency site from the command center;
dispatching from a UAV nest for the emergency site;
providing a visual alert from the light of the UAV;
transmitting data to the command center from the control center of the UAV; and
deploying traffic cones at the emergency site to reduce danger to emergency responders.

10. The method of claim 9, further comprising:
transporting to a nearby traffic location determined by the command center; and
presenting information on a display screen pertinent to nearby traffic.

* * * * *